US007596535B2

(12) United States Patent
de Voir et al.

(10) Patent No.: US 7,596,535 B2
(45) Date of Patent: Sep. 29, 2009

(54) APPARATUS FOR THE CLASSIFICATION OF PHYSIOLOGICAL EVENTS

(75) Inventors: Christopher S. de Voir, Tigard, OR (US); Richard A. Schomburg, Hillsboro, OR (US)

(73) Assignee: Biotronik GmbH & Co. KG (DE)

( * ) Notice: Subject to any disclaimer, the term of this patent is extended or adjusted under 35 U.S.C. 154(b) by 355 days.

(21) Appl. No.: 10/674,270

(22) Filed: Sep. 29, 2003

(65) Prior Publication Data

US 2005/0071303 A1 Mar. 31, 2005

(51) Int. Cl.
G06K 9/62 (2006.01)
G06K 9/64 (2006.01)
(52) U.S. Cl. .......................................... 706/20; 706/23
(58) Field of Classification Search .............. 706/20–23
See application file for complete search history.

(56) References Cited

U.S. PATENT DOCUMENTS

| | | | | | |
|---|---|---|---|---|---|
| 4,779,100 | A | * | 10/1988 | Voelz ..................... | 346/33 ME |
| 5,280,792 | A | * | 1/1994 | Leong et al. ................. | 600/515 |
| 5,299,284 | A | | 3/1994 | Roy | |
| 5,638,823 | A | | 6/1997 | Akay et al. | |
| 5,999,846 | A | | 12/1999 | Pardey et al. | |
| 6,105,015 | A | * | 8/2000 | Nguyen et al. ................. | 706/26 |
| 6,135,966 | A | | 10/2000 | Ko | |
| 6,192,273 | B1 | * | 2/2001 | Igel et al. ....................... | 607/14 |
| 6,287,328 | B1 | * | 9/2001 | Snyder et al. ................ | 600/509 |
| 6,393,316 | B1 | * | 5/2002 | Gillberg et al. ............. | 600/515 |
| 6,484,132 | B1 | * | 11/2002 | Hively et al. ................. | 702/190 |
| 6,594,524 | B2 | * | 7/2003 | Esteller et al. ................ | 607/45 |
| 6,658,287 | B1 | * | 12/2003 | Litt et al. .................... | 600/544 |
| 6,678,548 | B1 | * | 1/2004 | Echauz et al. ............... | 600/544 |

(Continued)

OTHER PUBLICATIONS

Dapos Alessandro, M. Esteller, R. Vachtsevanos, G. Hinson, A. Echauz, J. Litt, B., "Epileptic seizure prediction using hybrid feature selection over multiple intracranial EEG electrode contacts: a report of four patients", Biomedical Engineering, IEEE Transactions on, May 2003, vol. 50, Issue 5, pp. 603-615.*

(Continued)

Primary Examiner—David R Vincent
Assistant Examiner—Nathan H Brown, Jr.
(74) Attorney, Agent, or Firm—Hahn Loeser & Parks LLP (57) ABSTRACT

An apparatus according to the invention for the classification of physiological events has a signal input for the input of a physiological signal representing or constituting a physiological event and a classification unit 1 for classifying the physiological signal on the basis of its signal shape. The classification unit 1 includes a transformation unit 3 which is designed to carry out transformation of the physiological signal in such a way that as the output signal it outputs a number of values representing the physiological signal and based on the transformation; and a probabilistic neural network which is connected to the transformation unit 3 to receive the values and which contains a number of event classes which represent physiological events and which in turn are each represented by a set of comparative values, which probabilistic neural network is adapted on the basis of the comparison of the values with the comparative values to effect an association of the physiological signal represented by the values with one of the event classes.

5 Claims, 4 Drawing Sheets

U.S. PATENT DOCUMENTS

| | | | |
|---|---|---|---|
| 6,735,467 B2* | 5/2004 | Wilson | 600/544 |
| 6,898,582 B2* | 5/2005 | Lange | 706/14 |
| 2005/0070774 A1* | 3/2005 | Addison et al. | 600/323 |

OTHER PUBLICATIONS

Tian, et al, "Temporal Updating Scheme for Probabilistic Neural Network with Application to Satellite Cloud Classification," IEEE Transaction on Neural Networks, vol. 11 (No. 4), pp. 903-920, (Jul. 2000).

Burges, et al, "Improving Wavelet Image Compression with Neural Networks," www.research.microsoft.com, Microsoft Research (Redmond, WA), p. 1-17.

Dan Hammerstrom, "Working with Neural Networks," IEEE Spectrum, p. 46-53, (Jul. 1993).

Christopoulos, et al, "The JPEG2000 Still Image Coding System: An Overview," IEEE Transactions on Consumer Electronics, vol. 46 (No. 4), p. 1103-1127, (Nov. 2000).

F. Wang et al., Learning Structural Knowlege from the ECG, ISMDA 2001, LNCS2199, pp. 288-294, Springer-Verlag, Berlin Heidelberg, Germany.

M. Wiggins et al., Non-Invasive, Cardiac Risk Stratification Using Wavelet Coefficients, WSEAS Transactions on Computers, Bd. 2, Nr. 3, Jul. 2003, pp. 720-723.

A.S. Al-Fahoum et al., Combined wavelet transformation and radial basis networks for classifying life-threatening cardiac arrhythmias, Medical and Biological Engineering and Computing, Bd. 37, Nr. 5, Sep. 1999, Springer, Heidelberg, Germany.

Xuesong Ye et al., Noninvasive detection of coronary artery disease based on heart sounds, Engineering in Medicine and Biology Society, 1998, Proceedings of the 20th Annual International Conference of the IEEE Hong Kong, China Oct. 29-Nov. 1, 1998, Bd 3, 29, pp. 1546-1548, Piscataway, NJ, USA.

T.S. Leung et al., Classification of heart sounds using time-frequency method and artificial neural networks, Engineering in Medicine and Biology Society, 2000, Proceedings of the 22nd Annual International Conference of teh IEEE Jul. 23-28, 2000, Bd. 2, 23, pp. 988-991, Piscataway, NJ, USA.

R. O. Duda et al., Pattern Classification—PNNs and RBFs, Pattern Classification, Pager 172-173, 324-325, New Yourk, John Wiley & Sons, US.

European Search Report, European Application No. 04 09 0334, mailed Oct. 5, 2006.

* cited by examiner

APPARATUS FOR THE CLASSIFICATION OF PHYSIOLOGICAL EVENTS

The present invention concerns an apparatus for the classification of physiological events.

BACKGROUND OF THE ART

Physiological events give rise to physiological signals or themselves represent signals, on the basis of which they can be classified. The classification of physiological events or signals is useful in particular in relation to implantable medical devices such as for example cardiac pacemakers or implantable defibrillators in order to distinguish events requiring treatment from those which are not in need of treatment, or events in respect of which different treatments are indicated. On the basis of the classification procedure the implantable medical device is put into the position of automatically triggering off the treatment which is possibly required.

Previous apparatuses for the classification of physiological events, in particular intracardial events, in implantable medical devices are essentially based on filtering of the signal shape and on the provision of a threshold value or a plurality of threshold values in combination with time analysis in respect of the value exceeding/falling below the threshold value or values.

In order to achieve acceptable sensitivity to the signals of physiological events and acceptable distinguishability of events with the known apparatuses, it is necessary, during the cardiac cycle in which an event occurs, to suspend the recording of further physiological signals. However such suspension excludes the reliable detection of various important classes of intracardial events and the effective treatment thereof, thus for example an abnormal relationship between the two chambers of the heart.

Therefore the object of the present invention is to provide an improved apparatus for the classification of physiological events, in particular intracardial events, which helps to overcome the above specified disadvantages.

SUMMARY OF THE INVENTION

That object is attained by an apparatus for the classification of physiological events as set forth in claim 1. The appendant claims set forth advantageous configurations of the invention.

An apparatus according to the invention for the classification of physiological events has a signal input for the input of a physiological signal based on a physiological event or representing or constituting same and a classification unit for classifying the physiological signal on the basis of its signal shape. In the apparatus according to the invention the classification unit includes:

a transformation unit which is designed to carry out transformation of the physiological signal in such a way that as the output signal it outputs a number of values representing the physiological signal and based on the transformation; and a probabilistic neural network which is connected to the transformation unit to receive the values and which contains a number of event classes which represent physiological events (and which are typically implemented in the form of so-called nodes) and which in turn are each represented by a set of comparative values, wherein probabilistic neural networks are adapted on the basis of the comparison of the values with the comparative values to effect an association of the physiological signal represented by the values with one of the event classes.

Classification is therefore effected by the association of the physiological signal representing or constituting the physiological event with an event class. In that respect a physiological signal which prior to input into the classification unit is prepared, for example standardized, filtered, adjusted or converted in a similar fashion, is also to be considered as the physiological signal.

The combination of the transformation unit and the probabilistic neural network forms an effective classification unit for the classification of signals of intracardial events or other events or other signals of biological origin.

In a development of the invention the transformation unit is a transformation unit which is based on wavelet transformation, that is to say it is designed to implement the transformation operation on the basis of wavelets and a transformation rule which determines the values to be outputted using the wavelets.

Wavelet transformation is simple to perform and makes it possible to represent signals with relatively few values (coefficients). At the same time sufficient information is maintained about the signal in the event of wavelet transformation to guarantee reliable classification in the probabilistic neural network. In addition wavelet transformation affords the possibility of adapting the transformation within the mathematical limits which apply in respect of calculation of the transformation to the effective recognition of individual event classes.

The values obtained by means of the wavelet transformation operation preferably include values which describe a stem wavelet and additionally scaling values and translation values (coefficients) which in relation to a respective stem wavelet characterize the form of the input signal (physiological signal).

Comparability of the values and the comparative values in the probabilistic neural network is guaranteed to a particular extent if the comparative values are based on a transformation operation in which the same wavelets and the same transformation rule are used as in the transformation unit.

In an embodiment of the probabilistic neural network, for implementing the association of the physiological signal represented by the values with one of the event classes, the network includes:

at least one ascertaining unit for determining association probabilities of the physiological signal with the event classes on the basis of the comparison of the values with the comparative values of the respective event class and for outputting the ascertained association probabilities; and a selection unit which is connected to the ascertaining unit for receiving the association probabilities and which is adapted to extract the highest association probability from the association probabilities and to associate the physiological signal with the event class having the highest association probability.

In a development of the apparatus according to the invention, for an event class, there can be two or more sets of comparative values or coefficients representing the same event class. If such event classes are present, the ascertaining unit is adapted in particular for determining a plurality of association probabilities for each of those event classes. The selection unit is then designed in such a way that, for those event classes which have two or more sets of comparative values representing the same event class, the selection unit forms average values of the corresponding association probabilities and, upon extraction of the highest association probability, uses the average values instead of the individual values. The sensitivity of the apparatus to signal noise can be reduced with this development. The signal noise can result in classification errors and consequently in a lower degree of classification accuracy, in particular if there is a certain width of variation in physiological signals representing the same physiological event. With the above-mentioned development of the apparatus according to the invention, it is possible to take account of variations of that nature by means of various sets of comparative values, whereby the level of classification accuracy which is possible with a non-noisy signal is substantially maintained even in relation to those signals whose noise level would markedly reduce the level of classification accuracy, without having regard to the variations.

In the apparatus according to the invention, it is possible to connect upstream of the transformation unit an adjusting unit for centering the physiological signal in a time window of predetermined window width and for outputting the centered physiological signal to the transformation unit in order to achieve a unitary input format the physiological signals which occur. The above-mentioned variations in physiological signals which in themselves are the same, can occur in that respect for example in the form of offsets in the centering effect implemented by the adjusting unit. If such offsets remained disregarded, they would increase the sensitivity of the apparatus in relation to signal noise and thereby reduce the level of classification accuracy. In order to be able to take account of the offsets, it is therefore advantageous if, in those event classes which include two or more sets of comparative values representing the same event class, the sets of comparative values correspond to differing offsets in terms of centering of the centered physiological signal.

The apparatus according to the invention which can be implemented both in the form of hardware and also in the form of software is suitable in particular for use in an implantable medical device such as for example in a cardiac pacemaker or a defibrillator.

BRIEF DESCRIPTION OF THE DRAWINGS

Further features, properties and advantages of the present invention will be apparent from the description hereinafter of an embodiment with reference to the accompanying drawings in which.

DETAILED DESCRIPTION OF A PREFERRED EMBODIMENT

Figure 1:
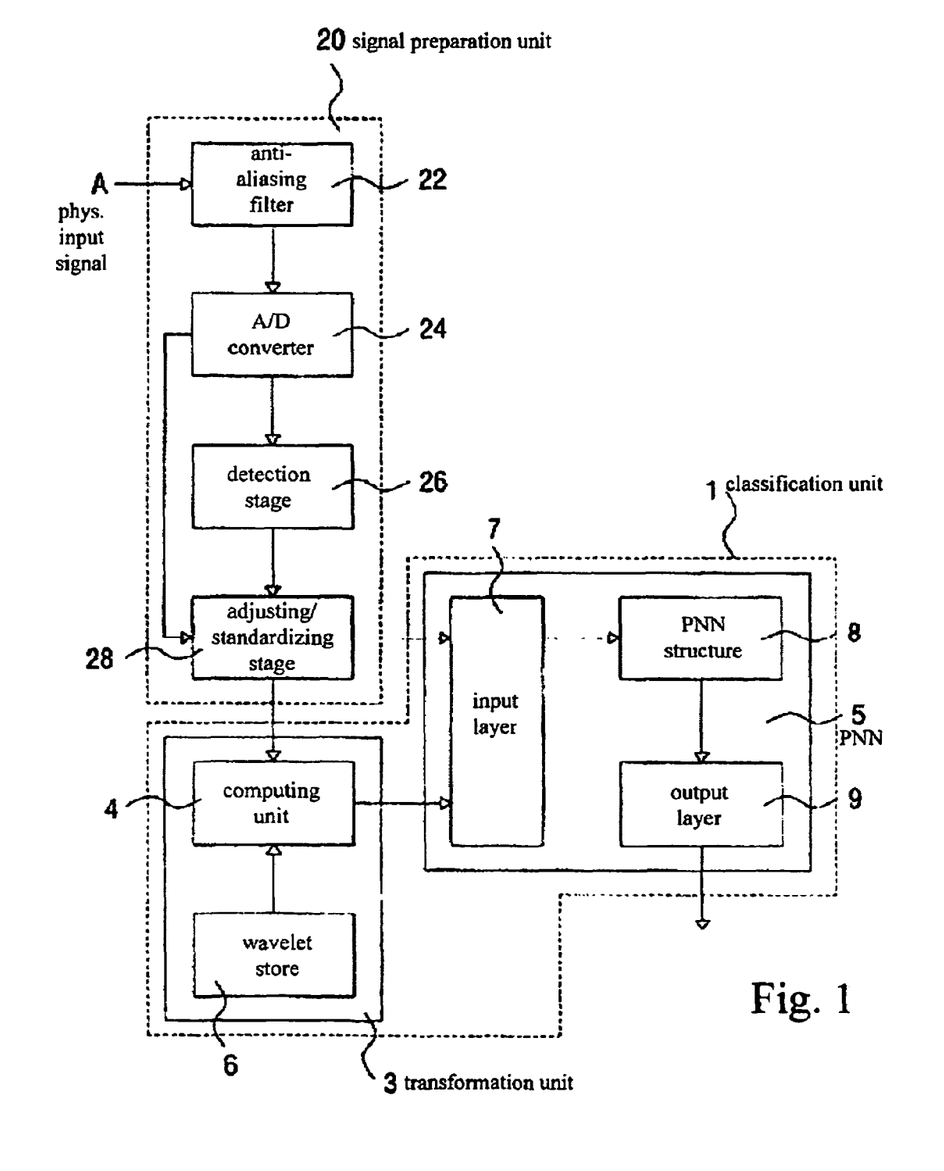
FIG. 1 shows an embodiment of the apparatus according to the present invention for the classification of physiological events.

FIG. 1 shows an embodiment of the apparatus according to the invention. The core of the apparatus according to the invention is formed by a classification unit 1 which includes a transformation unit 3 and a probabilistic neural network 5 which is connected to the transformation unit 3 for receiving coefficients (that is to say values) which represent a physiological signal which passes into the transformation unit 3 and is possibly processed therein. Connected upstream of the transformation unit 3 is a signal preparation unit 20 which in the present embodiment includes an anti-aliasing filter 22, a broadband analog-digital converter 24, referred to hereinafter for the sake of brevity as the A/D-converter, a detection stage 26 for the detection of a physiological event and a combined adjusting/standardizing stage 28, an incoming physiological input signal A passing through those stages in that sequence, the stage 28 being connected to the transformation unit to output a processed physiological signal.

Hereinafter, signal preparation, which is implemented in the signal preparation unit 20, of the physiological input signal A which in the present embodiment is an intracardial electrogram (IEGM), as is to be recorded for example by means of a cardiac pacemaker, will be briefly discussed. It should be pointed out however that the physiological signals which can be classified with the present invention are not limited to intracardial electrograms.

The anti-aliasing filter 22 involves filtering of the IEGM by means of an anti-aliasing low-pass filter as well as suitable amplification and/or scaling of the IEGM. As is known for sampled data systems, the filter suppresses signal components which can occur at frequencies above half the sampling rate and are superimposed by the subsequent signal processing steps. In addition no further filtering is effected to maintain the accuracy and the morphology of the signal shape of the IEGM.

The filtered IEGM is passed by the anti-aliasing filter 22 to the A/D converter 24 which is a conventional analog-digital converter with a stepwise linear relationship between the input signal and the output signal. The sampling rate and the resolution of the output signal are adapted to the demands of the classification procedure. In general they are at 1024 Hz or below or at 8 bits or above. Depending on the requirements involved it is possible to use various A/D-converter architectures, including the so-called "one-bit design". In special cases in which there are input signals with a large dynamic range, the use of nonlinear A/D-converter structures (which are companding, that is to say which compress the signal and then expand it again) may be advantageous. The converted IEGM is passed by the A/D-converter 24 as an output signal to the detection stage 26 and to the adjusting/standardizing stage 28.

The detection stage 26 involves the detection of an event on the basis of threshold consideration which is rate-adaptive from one event to another. The result of detection is indicated by an activity of the signal shape of the input signal. If the detection stage 26 detects an event it outputs a trigger signal (triggering signal) to the adjusting/standardizing stage 28 which triggers adjustment and/or standardization of the physiological signal.

If the adjusting/standardizing stage 28 receives a trigger signal from the detection stage 26, the underlying IEGM is detected in an event window with a predetermined window width which is generally 64 sampling steps, and centered in the window. The window is adapted to the expected type of event. The procedure also involves ascertaining the time interval from the last-detected event to the present event and standardization of the signal shape to a standardized peak-to-peak amplitude on the basis of a standardization factor in order to obtain a standardized event signal. The adjusting/standardizing stage 28 transmits the time interval and the standardization factor to the probabilistic neural network 5 whereas it transmits the event signal which is standardized and centered in the window to the transformation unit 3.

The transformation unit 3 executes wavelet transformation of the centered and standardized event signal, the result of the transformation operation being a number of coefficients representative of the signal. Wavelet transformation is a well-known method of compactly representing any signals. In that case, the transformation of a signal is effected by means of reference wavelets and a calculation procedure which specifies how the reference wavelets are to be calculated with the signal. Details of the transformation can be selected within the mathematical limits given by the calculation environment, in such a way that it can be highly effectively used for given signal classes. In the present embodiment which is intended for use in an implantable medical device, wavelet transformation makes it possible to represent an event window with a window width of 64 sampling steps (64-coefficient DWT) with fewer than 16 wavelet transformation coefficients and at the same time obtain sufficient information in respect of the signal, to guarantee reliable event classification in the probabilistic neural network 5.

For carrying out the wavelet transformation operation the transformation unit 3 includes a wavelet store 6 in which the reference wavelets are stored and a computing unit 4 which is connected to the adjusting/standardizing stage 28 for receiving the event signal standardized and centered in the window and to the wavelet store 6 for receiving the reference wavelets. Calculation of the coefficients, that is to say the actual wavelet transformation operation, takes place in the computing unit 4.

There are a number of calculation methods which are suitable for calculation of wavelet transformation. Equally there are a large number of suitable reference wavelets. For calculation of wavelet transformation in the computing unit 4, it is possible to select the set of reference wavelets used, for example having regard to the computing power which can be achieved. When selecting the calculation method and the reference wavelets however care is preferably to be taken to ensure that, when calculating wavelet transformation in the computing unit 4, the same calculation method and the same set of reference wavelets are used as are employed when calculating the comparative coefficients (see hereinafter).

The computing unit 4 outputs the result of wavelet transformation, that is to say the wavelet transformation coefficients, as a set of coefficients, to the probabilistic neural network 5 (abbreviated hereinafter to PNN).

The PNN 5 includes a PNN structure 8, an input layer 7 and an output layer or summation unit 9. The PNN structure 8 has a number of inner nodes and is connected to the input layer 7 which has a number of input nodes and to the summation unit 9 or output layer which has a number of output nodes.

The inner nodes of the PNN structure 8 each contain a given coefficient vector which contains comparative coefficients as a set of comparative values, a given comparative time interval and a given comparative standardization factor, and characterizes a given class of events. In the preferred embodiment the PNN structure 8 includes for each class just one node, but it is also possible to associate with a class a plurality of inner nodes with respective slightly different coefficient vectors so that a class is represented by a node cluster. The coefficient vectors are usually previously extracted from a plurality of signals of the signal shape which is typical for the event class.

The purpose of the input layer 7 of the PNN 5 is to receive the coefficients from the transformation unit 3 and the time interval and the standardization factor of the present IEGM from the adjusting/standardizing stage 28 and to distribute them uniformly over the inner nodes of the PNN structure 8.

In the inner nodes the respective coefficient vectors are compared to a signal vector which is formed from the coefficients received from the transformation unit 3, as well as the time interval and the standardization factor of the present IEGM, by forming the difference of the signal vector and the coefficient vector. In addition, probability values are associated with the ascertained vector differences, in which respect the probability value is greater in proportion to a decreasing vector difference. The operation of determining the probability values can include a Gaussian transfer function with selectable standard deviation sigma (which specifies the spacing of the points of inflexion of the curve from the center of the curve). The selectable standard deviation makes it possible to establish the limits, that is to say the maximum admissible deviation from the respective standard signal shape of a class.

The PNN structure 8 is connected to the summation unit 9 for transmitting the signal vector and the probability values ascertained for the signal vector.

The summation unit 9 has precisely one output node for each event class, for the recognition of which the apparatus according to the invention is designed. The output node receives the probability value of the signal vector, which is ascertained for the respective event class. If a plurality of inner nodes are associated with an event class, the corresponding output node receives all probability values of those inner nodes and calculates the average value of the corresponding probability values. In both cases the probability value of an output node of the summation unit 9 represents the probability of the IEGM or the triggering event belonging to the class represented by the output node. The event triggering the IEGM is associated with that class which involves the highest probability value in the summation unit 9, insofar as that probability value exceeds a classification threshold. If it does not exceed the classification threshold the event is classified as unknown and possibly used to trigger adaptation of the PNN structure, which results in recognition of a new event class. Finally the summation unit 9 outputs the signal vector and the event class with which it has been associated as the result of the classification procedure.

As stated above a node of the PNN structure 8 includes a predetermined coefficient vector which characterizes the event class represented by the node. As those coefficient vectors of an event class have been extracted to start with from a representative amount of signals which go back to the corresponding event class, it is not to be expected that such a coefficient vector exactly reproduces an individual input signal to be classified. Accordingly classification is effected in the apparatus according to the invention on the basis of the similarity between the signal vector which goes back to the input signal and in which the information concealed in the input signal is encoded and the coefficient vectors of the nodes.

The information concealed in the input signal is encoded after preparation of the input signal in the signal processing unit 20 in the transformation unit 3 by means of the wavelet transformation procedure. Wavelet transformation however is not invariant in relation to a time shift in the input signal in the signal window, that is to say the result of transformation changes if the maximum of the amplitude is moved forward or back by one or more sampling steps in the signal window. Consequently the values of the coefficients which are outputted by the transformation unit and which are of substantial significance for classification can fluctuate. The degree of fluctuation depends on the accuracy of centering of the input signal in the signal window. Although the direct effect of that fluctuation on the classification procedure is generally slight, significant classification errors can occur if noisy input signals are involved.

Hereinafter classification implemented by means of the apparatus according to the invention is described with reference to FIGS. 2 through 6 representing intermediate steps in the course of the classification procedure, on the basis of two different test input signals by way of example. The test signals involved are on the one hand a sine-like so called Haversine signal and on the other hand a triangular signal. In this respect in particular the concepts involved in reducing the influence of factors which worsen the level of classification accuracy will be explained.

Figure 2:
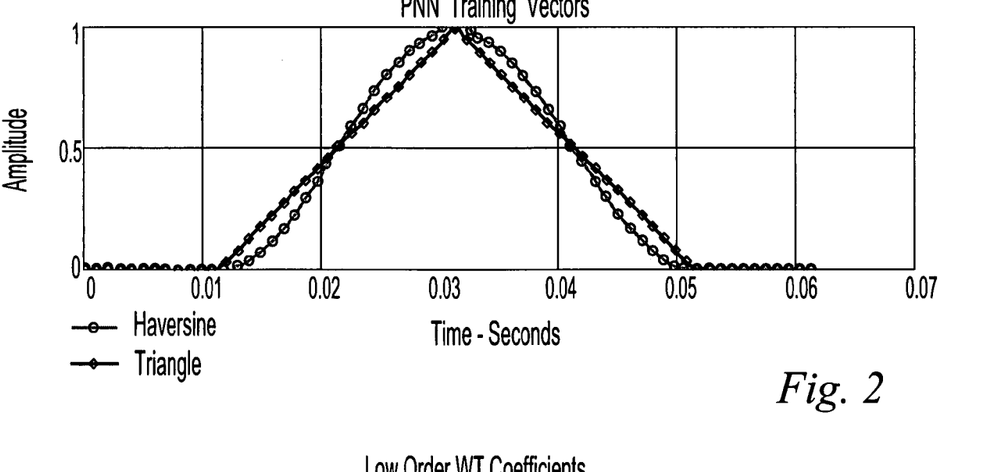
FIG. 2 shows a pair of test signals, on the basis of which the mode of operation of the apparatus according to the invention is described.

FIG. 2 shows the Haversine signal and the triangular signal which are to be distinguished with the apparatus according to the invention as a function of time. For both signals, the signal duration is 40 ms, the peak amplitude is 1 V and the sampling rate is 1024 per second. The basic shape of the two signals is similar to usual signal shapes of intracardial electrograms.

Figure 3:
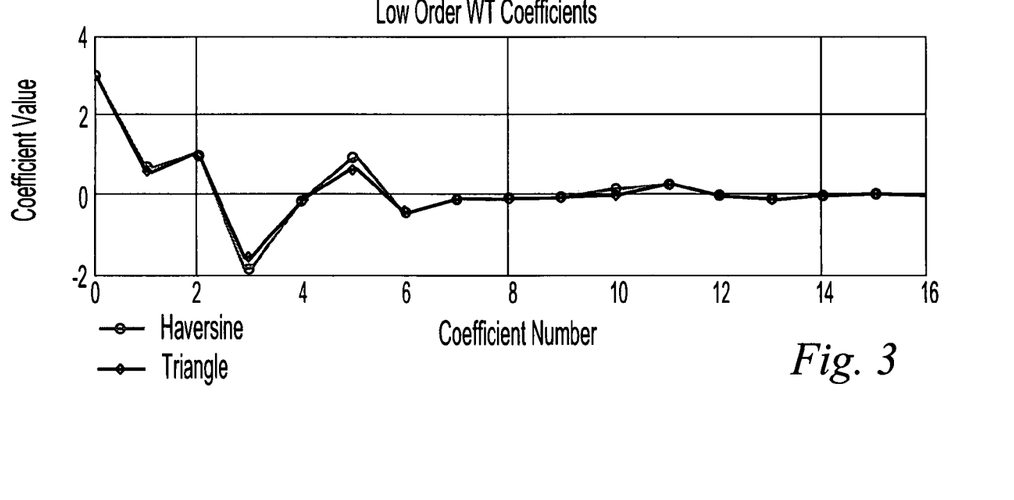
FIG. 3 shows the coefficients, obtained by means of wavelet transformation, of the two test signals shown in FIG. 2.

FIG. 3 shows the low order coefficients which were obtained for the Haversine signal and the triangular signal respectively in the transformation unit 3 by means of wavelet transformation. This procedure involved the use of a Daubechies-4-transformation procedure as the wavelet transformation procedure, which was applied in each case to a Haversine signal and a triangular signal respectively which has been previously centered in a signal window of a width of 64 sampling steps. Admittedly, the similarities between the respective coefficients are great, but sufficient differences are to be noted between the coefficients. Other wavelet transformation procedures lead to be similar results as the Daubechies-4-transformation procedure.

Figure 4:
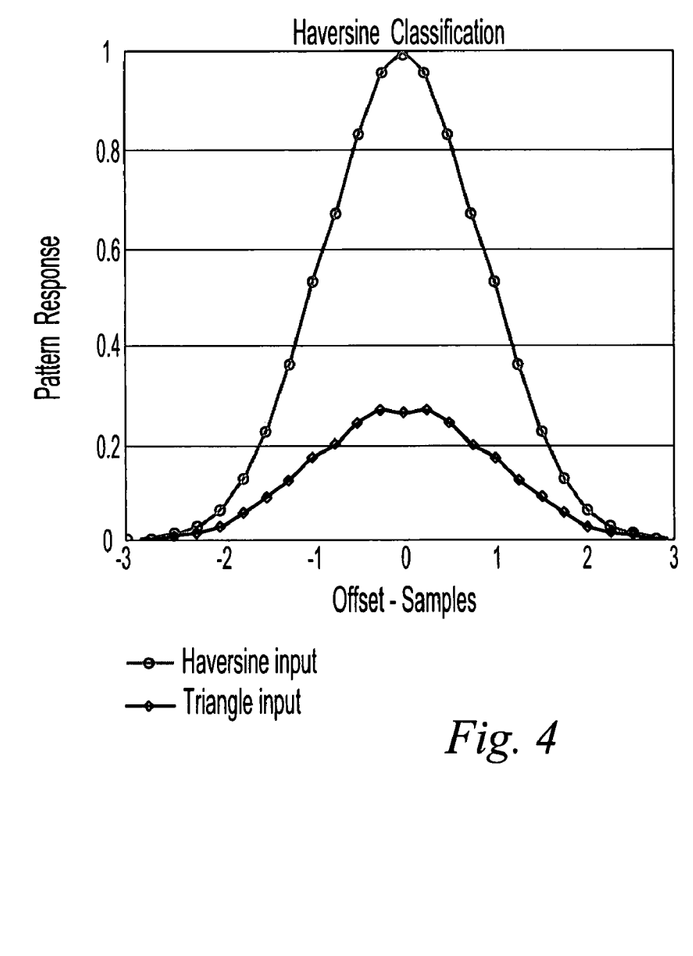
FIG. 4 shows the effect that an offset in centering of the two test signals in a time window has on the classification result.

FIG. 4 shows both in respect of the Haversine signal and also in respect of the triangular signal the effects which various offsets (measured in sampling steps) leave behind upon centering of the signal in the signal window in a node of the PNN structure 8 with a coefficient vector representing a Haversine signal (that is to say the node is adapted to represent an event class which leads to a Haversine signal).

In the situation involving perfect centering of the signal in the signal window, that is to say in the case of an offset of the value zero, the node which represents the Haversine signal outputs an output value 1 for the Haversine signal as the input signal and an output value of about 0.25 for the triangular signal as the input signal. If on the other hand there is an offset by a sampling step in respect of centering of the Haversine signal or the triangular signal respectively in the signal window (offset +1 or −1), then the output value for the Haversine signal as the input signal is reduced to about 0.55 and that for the triangular signal as the input signal is reduced to about 0.18.

The difference between the two output values shown in FIG. 4 forms the basis of event classification by means of the probabilistic neural network 5. In that respect a great difference (as in the case of the offset 0) ensures a low level of susceptibility of the classification procedure in relation to signal noise. The reduction in difference by virtue of the offset of +1 or −1 (measured in sampling steps) to approximately half the value with an offset of zero has the result that, in the case of the offset of +1 or −1 respectively classification errors already occur at noise levels which are half as high as the noise level at which classification errors occur with an offset of zero. That can result in a significant reduction in the operational efficiency of the apparatus, in many uses.

As already mentioned it is possible for a plurality of inner nodes with respective slightly different coefficient vectors to be associated in the PNN structure 8 with an event class so that an event class is represented by a node cluster. The node cluster can now be of such a nature that associated with an event class are two or more nodes which each contain a respective coefficient vector corresponding to a (preferably slight) offset in the input signal to be expected. The coefficient vectors are usually extracted to start with from a plurality of signals involving the signal shape which is typical for the event class, wherein the signals for various nodes of a node cluster are (slightly) displaced in respect of time relative to each other, that is to say they have an offset. In that respect the magnitude of the time displacement can be selected having regard to the offset to be expected in the input signal, that is to say the level of accuracy to be expected in centering of the input signal in the signal window.

Figure 5:
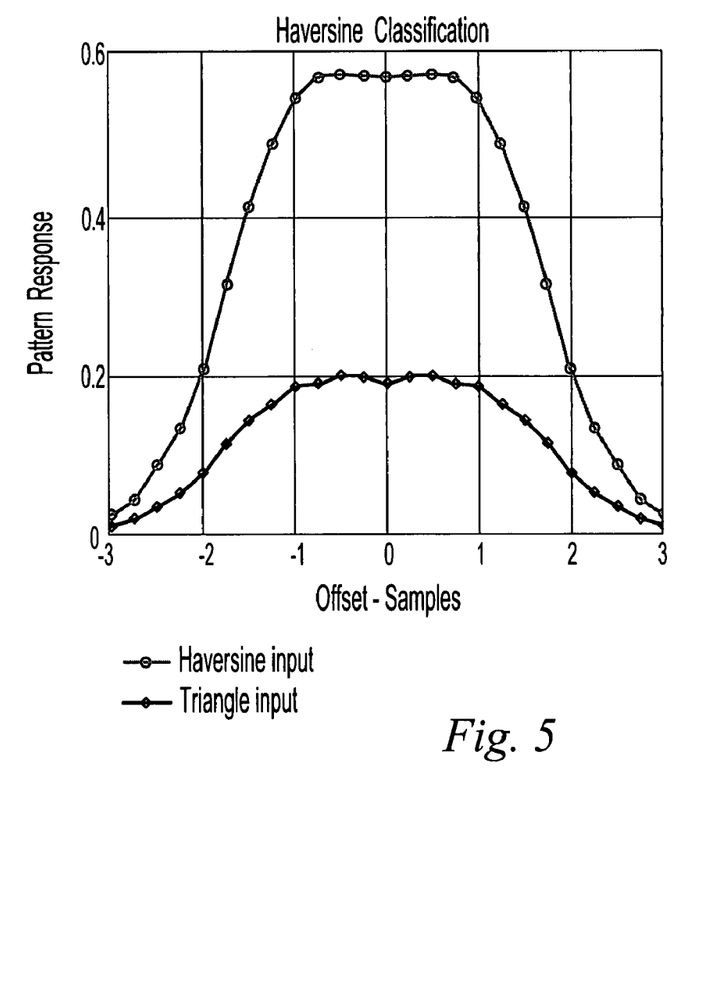
FIG. 5 shows the effect that an offset in centering of the two test signals in a time window has on the classification result, if offsets are taken into consideration by means of two or more sets of comparative coefficients representing the same event class.
Figure 6:
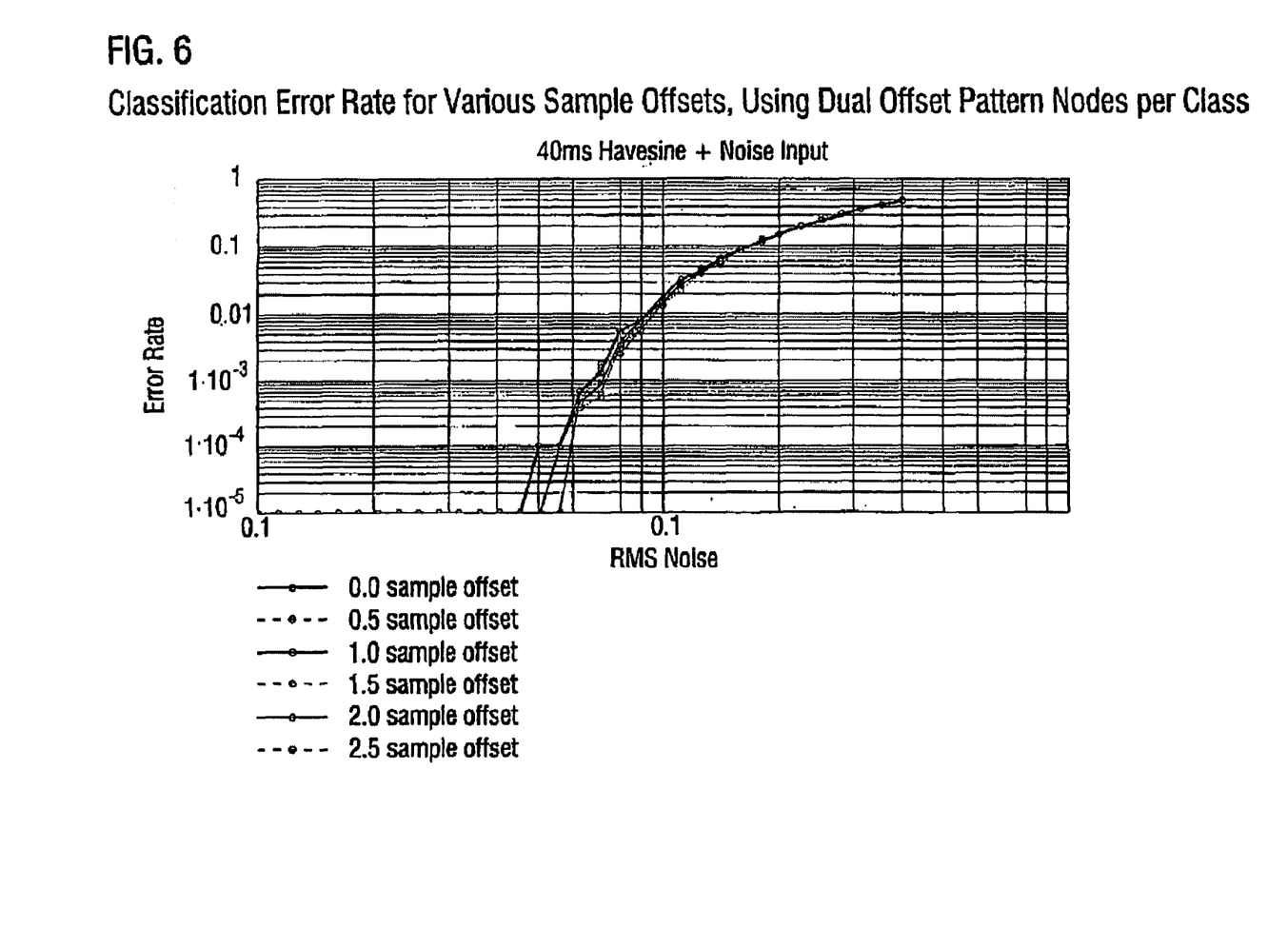
FIG. 6 shows the error rate in the classification procedure for various offsets occurring upon centering in the time window in dependence on the signal noise.

Accordingly a node cluster of that kind provides an enlarged range in which there is a high difference between its output value in the case of a Haversine signal as the input signal and its output value in the case of a triangular signal as the input signal (FIG. 5). In that way it is possible to maintain a high level of classification accuracy even with noise levels which would otherwise significantly influence the degree of classification accuracy. The pattern of the error rate upon classification in a node cluster representing a Haversine signal is shown in FIG. 6 for various offsets occurring upon centering in the time window, in dependence on the signal noise.

The invention claimed is:

1. An apparatus for the classification of physiological events, comprising:
   a signal input for the input of a physiological signal representing or constituting a physiological event;
   a classification unit for classifying the physiological signal on the basis of its signal shape, the classification unit comprising:
      a transformation unit which is designed to carry out transformation of the physiological signal in such a way that it outputs a number of values representing the physiological signal and based on the transformation; and
      a probabilistic neural network which is connected to the transformation unit to receive the values and which contains a number of event classes which represent physiological events and which in turn are each represented by a set of comparative values, which probabilistic neural network is adapted on the basis of the comparison of the values with the comparative values to effect an association of the physiological signal represented by the values with one of the event classes, wherein the probabilistic neural network further comprises,
         at least one ascertaining unit for determining association probabilities of the physiological signal with the event classes on the basis of the comparison of the values with the comparative values of the respective event class and for outputting the ascertained association probabilities, and
         a selection unit which is connected to the ascertaining unit for receiving the association probabilities and which is adapted to extract the highest association probability from the association probabilities and to associate the physiological signal with the event class having the highest association probability,
         and wherein two or more sets of comparative values representing the same event class are present for at least one event class, and wherein the ascertaining unit is adapted to determine a plurality of association probabilities for each event class which has two or more sets of comparative values representing the same event class, and the selection unit is so designed that, for those event classes which have two or more sets of comparative values representing the same event class, it forms average values of the corresponding association probabilities and upon extraction of the highest association probability uses the average values instead of the individual values; and an adjusting unit for automatically time-centering the physiological signal with respect to the time dimension in a time window of predetermined window width in said time dimension, and for outputting the time-centered physiological signal to the transformation unit, the adjusting unit connected upstream of the transformation unit, and wherein in those event classes which include two or more sets of comparative values representing the same event class, the sets of comparative values correspond to different offsets in the centering of the centered physiological signal.

2. The apparatus of claim 1, wherein:
the transformation unit is adapted for executing the transformation operation on the basis of wavelets and a transformation rule determining the values to be outputted using the wavelets.

3. The apparatus of claim 2, wherein:
the comparative values of the probabilistic neural network are based on a transformation procedure in which the same wavelets and the same transformation rule as in the transformation unit are used.

4. An implantable medical device characterized in that it is provided with an apparatus for the classification of physiological events as set forth in claim 1.

5. The implantable medical device of claim 4, wherein:
the implantable medical device is in the form of a cardiac pacemaker or defibrillator.

* * * * *